(12) United States Patent
Baïkoff (10) Patent No.: US 7,347,554 B2
(45) Date of Patent: Mar. 25, 2008

(54) DETERMINING CRITERIA FOR PHAKIC INTRAOCULAR LENS IMPLANT PROCEDURES

(75) Inventor: Georges Baïkoff, Marseilles (FR)

(73) Assignee: Carl Zeiss Meditec, Inc., Dublin, CA (US)

( * ) Notice: Subject to any disclaimer, the term of this patent is extended or adjusted under 35 U.S.C. 154(b) by 329 days.

(21) Appl. No.: 11/080,354

(22) Filed: Mar. 15, 2005

(65) Prior Publication Data
US 2006/0209259 A1 Sep. 21, 2006

(51) Int. Cl.
*A61B 3/00* (2006.01)
*G02C 7/04* (2006.01)

(52) U.S. Cl. .................... 351/246; 351/160 R
(58) Field of Classification Search .......... 351/246
See application file for complete search history.

(56) References Cited

U.S. PATENT DOCUMENTS

| | | | | |
|---|---|---|---|---|
| 5,555,039 | A * | 9/1996 | Iki et al. ............ | 351/205 |
| 5,838,811 | A * | 11/1998 | Lindmark .......... | 382/100 |
| 5,968,095 | A * | 10/1999 | Norrby ............. | 128/898 |
| 6,004,314 | A * | 12/1999 | Wei et al. ......... | 606/12 |
| 6,231,186 | B1 * | 5/2001 | Broadus et al. .... | 351/208 |
| 6,442,409 | B1 * | 8/2002 | Peyman ............ | 600/318 |
| 6,478,821 | B1 * | 11/2002 | Laguette et al. ... | 623/6.49 |
| 2003/0018386 | A1 * | 1/2003 | Laguette et al. ... | 623/6.46 |
| 2005/0018137 | A1 * | 1/2005 | Barth et al. ....... | 351/221 |

OTHER PUBLICATIONS

G. Baïkoff et al. "Crystalline Lens' Rise: A New Safety Criterion For Phakic Artisan Implants. An AC OCT Study"; *J. Cataract and Refract Surg*; Apr. 10, 2004, pp. 1-26.
S.N. Fedorov et al. "Intraocular correction of high myopia"; *Vestn Oftalmol*; 104: 14-16; 1988 Russian with English Summary).
P.U. Fechner et al. "The Correction of Myopia by Lens Implantation Into Phakic Eyes"; *Am J Opthalmol*; 107: 659-63; Jun. 1989.
G. Baïkoff et al. "Comparison of Minus Power Anterior Chamber Intraocular Lenses and Myopic Epikeratoplasty in Phakic Eyes"; *Refract & Corneal Surg*; 6: 252-260; Jul./Aug. 1990.
D. Huang et al. "Optical Coherence Tomography"; *Science*; 254: 1178-81; 1991.
J.A. Izatt et al. "Micrometer-Scale Resolution Imaging of the Anterior Eye In Vivo With Optical Coherence Tomography"; *Arch Ophthalmology*; 112: 1584-89, Dec. 1994.
C. Puliafito et al. "Optical Coherence Tomography of Ocular Diseases"; Slack Inc.; 1996; pp. 3-15.
P.U. Fechner et al. "Iris-claw lens in phakic eyes to correct hyperopia: Preliminary study"; *J Cataract Refract Surg*; 24: 48-56; 1998.

(Continued)

Primary Examiner—Scott J. Sugarman
Assistant Examiner—DaWayne A Pinkney
(74) Attorney, Agent, or Firm—Michael B. Einschlag (57) ABSTRACT

One embodiment of the present invention is a method for determining whether to perform a phakic intraocular lens implant procedure, which method includes: (a) obtaining an image of an anterior segment of an eye; (b) determining a distance from a crystalline lens to another part of an anterior chamber from the image; and (c) comparing the distance with a predetermined value.

10 Claims, 9 Drawing Sheets

OTHER PUBLICATIONS

T.H. Neuhann "International ICL Study. Results and Personal Technique": [C.F. Lovisolo et al., Eds.] "The Implantable Contact Lens (ICL™) and Other Phakic IOLs" F. Canelli, Editore s.r.l.; Chap. 22, pp. 319-327; 1999.

R. Zaldivar et al. "ICL™: Our Experience"; [C.F. Lovisolo et al., Eds.] "The Implantable Contact Lens (ICL™) and Other Phakic IOLs" F. Canelli Editore s.r.l.; Chap. 24, pp. 339-360; 1999.

D.D. Dementiev et al. "Phakic Refractrive Lens for Correction of Myopia and Hyperopia"; in [S. Agarwal et al., Eds.] "Refractive Surgery"; New Delhi, Jaypee Brothers; Chap. 41, pp. 441-461; 2000.

S. Radhakrishnan et al. "Real-Time Optical Cohenrence Tomography of the Anterior Segment at 1310nm"; *Arch Ophthalmology*; vol. 119, pp. 1179-1185; Aug. 2001.

J.L. Alio et al. "Artisan Phakic Iris Claw Intraocular Lens for High Primary and Secondary Hyperopia"; *J Refract Surg*; 18(6): 697-707; Nov./Dec. 2002.

I.F. Comaish et al. "Phakic intraocular lenses"; *Curr Opin Ophthalmol*; 13: 7-13; 2002.

M. Gonvers et al. "Implantable contact lens for moderate to high myopia: Relationship of vaulting to cataract formation"; *J Cataract Refract Surg*; vol. 29 pp. 918-924; May 2003.

R. Saxena et al. "Three-year Follow up of the Artisan Phakic Intraocular Lens for Hypermetropia"; *Ophthalmology*; vol. 110, No. 7, pp. 1391-1395; Jul. 2003.

C. Wirbelauer et al. "Experimental Imaging of Intracorneal Ring Segments with Optical Coherence Tomography" *J Refract Surg*; 19: 367-71; May/Jun. 2003.

C. Wirbelauer et al. "Intraoperative Optical Coherence Pachymetry During Laser in situ Keratomileusis—First Clinical Experience"; *J Refract. Surg*; 19: 372-77; May/Jun. 2003.

C. Wirbelauer et al. "Imaging scleral expansion bands for presbyopia with optical coherence tomography"; *J Cataract Refract Surg*; 29: 2435-38, 2003.

J.L. Alio et al. "Surgical Correction of High Degrees of Astigmatism with a Phakic Toric-Iris Claw Intraocular Lens"; *Int Ophthalmol Clin* 43(3): pp. 171-181, 2003.

J.F. Koretz et al. "Scheimpflug and high-resolution magnetic resonance imaging of the anterior segment: a comparative study"; *J Opt Soc Am A*; vol. 21, No. 3. pp. 346-354; Mar. 2004.

G. Baïkoff et al. "Static and dynamic analysis of the anterior segment with optical coherence tomography study"; *J Cataract Refract Surg*; 30: 1843-1850; Sep. 2004.

G. Baïkoff et al. "Contact between 3 phakic intraocular lens models and the crystalline lens: An anterior chamber optical coherence tomography study"; *J Cataract Refract Surg*; 30: 2007-2012; Sep. 2004.

G. Baïkoff et al. "Assessment of capsular block syndrome with anterior segment optical coherence tomography"; *J Cataract Refract Surg*; vol. 30, pp. 2448-2450, Nov. 2004.

G. Baïkoff "The GBR/VIVARTE Presbyopic Foldable Phakic IOL"; [J.L. Alio et al., Eds.] "Refractive Surgery with Phakic IOLs. Fundamentals and Clinical Practice"; Panama; Chap. 15, pp. 207-217; 2004.

S. Purohit et al. "Angle Supported Phakic Intraocular lens: The Phakic 6H2"; in [D.R. Hardten et al. Eds.] "Phakic Intraocular Lenses. Principles and Practice"; Slack Inc.; Chap. 16, pp. 163-169, 2004.

T. Kohnen et al. "Complications of Phakic Intraocular Lenses"; [D. Hardten et al. Eds.] "Phakic Intraocular Lenses. Principles and Practice"; Slack Inc.; Chap. 9, pp. 81-96; 2004.

M.M. Braun et al. "The Artisan Phakic Intraocular Lens"; in [D. Hardten et al. Eds.]; "Phakic Intraocular Lenses, Principles and Practice"; Slack Inc.; Chap. 13, pp. 133-143, 2004 Ophtec Website: www.ophtec.com.

S. Leroux les Jardins et al. "Optical Biometry of High Myopic Eyes Corrected by Phakic IOL" oral presentation during an AAO Refractive Surgery Subspecialty Day Meeting in Anaheim, California No. AM0829 on Nov. 15, 2003 -presentation on an AAO CDROM- photos of slides presented.

* cited by examiner

DETERMINING CRITERIA FOR PHAKIC INTRAOCULAR LENS IMPLANT PROCEDURES

TECHNICAL FIELD OF THE INVENTION

One or more embodiments of the present invention relate generally to methods for determining criteria for use in determining whether to perform phakic intraocular lens implant procedures.

BACKGROUND OF THE INVENTION

Use of phakic implants for correcting high myopia was discussed in the 1950s and 1960s, but was not implemented because of technological difficulties. It was reintroduced later by various groups, for example, one may refer to an article by P. U. Fechner, G. L. van der Heijde, and J. G. F. Worst entitled "The Correction of Myopia by Lens Implantation Into Phakic Eyes" in *Am J Ophthalmol*, 107: 659-63, June 1989; an article by S. N. Fedorov, V. K. Zuyev, and E. R. Turnanyan entitled "Intraocular correction of high myopia" in *Vestn Oftalmol*, 104: 14-16, 1988; and an article by G. Baïkoff and P. Joly entitled "Comparison of Minus Power Anterior Chamber Intraocular Lenses and Myopic Epikeratoplasty in Phakic Eyes" in *Refract & Corneal Surg*, 6: 252-260, July/August 1990. The use of phakic implants for correcting hyperopia was only envisaged later because most believed that a hyperope's anterior chamber was too shallow for this type of procedure.

More recently, toric implants (for example, toric implants available under the trademarks ICL™ and ARTISAN™) have been proposed to correct astigmatism, for example, one may refer to an article by T. H. Neuhann entitled "International ICL study" in [C. F. Lovisolo and P. M. Pesando, Eds.] "The Implantable Contact Lens (ICL™) and Other Phakic IOLs" F. Canelli, Editore s.r.l., pp. 319-328, 1999; and an article by J. L. Alio, A. Galal, and E. Mulet in "Surgical correction of high degrees of astigmatism with a phakic toric iris-claw intraocular lens" *Int Ophthalmol Clin* 43(3): pp. 171-81, 2003. In addition, it is only recently that multifocal phakic implants (for example, multifocal phakic implants available under the trademarks NEWLIFE™ and VIVARTE Presbyopic™) are being used to correct presbyopia, for example, one may refer to an article by G. Baïkoff entitled "The GBR/VIVARTE Presbyopic Foldable Phakic IOL" in [J. L. Alio and J. J. Perez-Santonja, Eds.] "Refractive Surgery with Phakic IOLs. Fundamentals and Clinical Practice" Panama, 2004, at p. 207-217. In fact, only the following phakic IOL implants have obtained a CE mark for correction of hyperopia: (a) posterior chamber phakic IOL implants available under the trademarks ICL™ and PRL™ (for example, one may refer to an article by R. Zaldivar, M. J. Davidorf, and S. Oscherow entitled "The Intraocular Contact Lens" in [C. F. Lovisolo and P. M. Pesando, Eds.] "The Implantable Contact Lens (ICL™) and Other Phakic IOLs" F. Canelli, Editore s.r.l., 1999, pp. 339-360 and an article by D. D. Dementiev et al. entitled "Phakic Refractive Lens for Correction of Myopia and Hyperopia" in [S. Agarwal, A. Agarwal, I. G. Pallikaris, T. H. Neuhann, and M. C. Knorz, Eds.] "Refractive Surgery" New Delhi, Jaypee Brothers, 2000, pp. 441-461); (b) iris fixated implants available under the trademarks ARTISAN™ and VERISYSE™ (for example, one may refer to an article by P. U. Fechner, D. Singh and K. Wulff entitled "Iris-claw lens in phakic eyes to correct hyperopia: Preliminary study" in *J Cataract Refract Surg*, 24: 48-56, 1988); and (c) angle supported implants available under the trademark PHAKIC 6™ (for example, one may refer to an article by S. Purohit et al. entitled "Angle supported Phakic Intraocular lens: The Phakic 6H2" in [D. R. Hardten, R. L. Lindstrom, and E. A. Davis, Eds.] "Phakic Intraocular Lenses. Principles and Practice" Slack Inc., 2004).

The inventor has had experience with spherical ARTISAN™ IOL implants consisting of two-hundred-seventy-three (273) IOL implants being inserted into one-hundred-thirty-seven (137) myopic and one-hundred-thirty-six (136) hyperopic eyes. In this series of procedures, it was observed that nine (9) eyes developed pigment dispersion; a surprisingly high number given that attention had been paid to indications and contraindications recommended by Ophtec (refer to its web site at www.ophtec.com) and identified in an article by R. Saxena, M. Landesz, B. Noordzij, and G. P. M. Luyten entitled "Three-year Follow-up of the Artisan Phakic Intraocular Lens for Hypermetropia" in *Ophthalmology*, Vol. 110, No. 7, pp. 1391-95, July 2003. These recommendations included having an anterior chamber depth (i.e., a distance between the crystalline lens' anterior pole and the corneal epithelium as measured on a median of a base line joining angle recess to angle recess) of at least 2.9 mm. In addition, the implant procedure was not performed on irises that were "too convex." After carrying out a biomicroscopic analysis of the ARTISAN™ IOL implants, it appeared that the iris seemed to be sandwiched between the crystalline lens and the implant in the cases of pigment dispersion. As a result, it was concluded that these results were caused by an abnormal forward position of the crystalline lens in these patients, and the shape and convexity of the iris merely provided a qualitative criterion.

In light of the above, there is a need in the art for a method for determining criteria for use in determining whether to perform phakic lens implant procedures to prevent, among other things, development of pigment dispersion in an implanted eye.

SUMMARY OF THE INVENTION

One or more embodiments of the present invention satisfy one or more of the above-identified needs in the art. In particular, one embodiment of the present invention is a method for determining whether to perform a phakic intraocular lens implant procedure, which method comprises: (a) obtaining an image of an anterior segment of an eye; (b) determining a distance from a crystalline lens to another part of an anterior chamber from the image; and (c) comparing the distance with a predetermined value.

DETAILED DESCRIPTION

In accordance with one or more embodiments of the present invention, a crystalline lens height is an anatomical reference that may be utilized to provide a quantitative criterion for use in determining whether to perform phakic lens implant procedures to prevent, among other things, development of pigment dispersion in an implanted eye. Further, and as will be described in detail below, in accordance with one or more embodiments of the present invention, the crystalline lens height can be determined readily from an image of an anterior segment of an eye that is obtained utilizing any one of a number of methods that are known to those of ordinary skill in the art.

Figure 1:
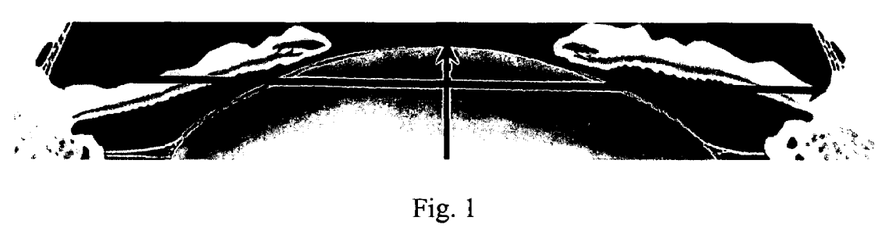
FIG. 1 shows an image of an anterior segment of an eye wherein a crystalline lens height is determined in accordance with one or more embodiments of the present invention, the crystalline lens height being defined as a distance between an anterior pole of the crystalline lens and a horizontal plane joining opposite irido-corneal recesses (more specifically, a line connecting a 3:00 o'clock angle recess and a 9:00 o'clock angle recess of a patient's eye wherein this distance is measured on the anterior segment's horizontal diameter median)

FIG. 1 shows an image of an anterior segment of an eye wherein a crystalline lens height is determined in accordance with one or more embodiments of the present invention. As shown in FIG. 1, the crystalline lens height is defined as a distance between an anterior pole of the crystalline lens and a horizontal plane joining opposite irido-corneal recesses (more specifically, a line connecting a 3:00 o'clock angle recess and a 9:00 o'clock angle recess of a patient's eye wherein this distance is measured on the anterior segment's horizontal diameter median). Advantageously, and in accordance with the present invention, the crystalline lens height provides an objective criterion because, as the iris fits tightly against the crystalline lens, its shape will depend on the position of the crystalline lens' anterior pole with respect to the iris root.

Biometric measurements of eighty-seven (87) eyes with an ARTISAN™ IOL implant have been analyzed, and a comparative analysis of crystalline lens height was carried out on nine (9) eyes having developed pigment dispersion and seventy-eight (78) eyes without any problems using an anterior chamber optical coherence tomography (AC OCT) equipment. This analysis shows that crystalline lens height can be used as a quantitative criterion for use in determining whether to perform phakic lens implant procedures to prevent, among other things, development of pigment dispersion in an implanted eye—using ARTISAN™ IOL implants or other type of phakic lens implants. Indeed, the higher the crystalline lens height, the greater the risk of developing pigment dispersion in the pupil area. In addition, this complication (i.e., pigment dispersion) is more frequent in hyperopes than in myopes. Thus, in accordance with one or more embodiments of the present invention, there is little or no risk of pigment dispersion if the crystalline lens height is below 600 μm, however there is a higher risk whenever the crystalline lens height is ≧600 μm where there may be as much as a 67% rate of pupillary pigment dispersion. In addition, in certain cases when the IOL implant is loosely fixed, and there is no traction on the iris root, this complication (i.e., pigment dispersion) can be avoided or delayed. In particular, in accordance with one or more embodiments of the present invention, and as will be described in detail below, a distance remaining between the crystalline lens height and a 600 μm safety level can be utilized to calculate a tolerance safety period of time for an IOL implant.

As is well known, the following medical imaging systems provide complete cross-sectional images of the anterior segment of an eye along the eye's anterior-posterior axis: (a) images obtained by ultra high frequency (UHF) ultrasound scan equipment (for example, an ultrasound scan provided by equipment available from Artemis); (b) images obtained using a Scheimpflug technique (for example Scheimpflug photos provided by Nidek's EAS equipment and by Oculus' Pentacam equipment—although the angle recess is not visible with the Scheimpflug technique such as that provided by Nidek's EAS or Oculus' PENTACAM); (c) images provided by anterior segment optical coherence tomography (AC OCT) equipment (for example, AC OCT equipment developed by Carl Zeiss Meditec); and (d) images provided by magnetic resonance imaging or the tomodensitometry equipment. Because ultrasound B and UBM scanning techniques do not provide a one-step image of the anterior segment, and require geometric reconstructions that are likely to induce errors, and the MRI techniques or tomodensitometry techniques are not suitable for routine clinical usage, it is preferred to obtain images using AC OCT equipment, for example, 1310 nm AC OCT equipment. OCT equipment using an 820 nm wavelength are well-known posterior segment imaging devices (see an article by D. Huang et al. entitled "Optical Coherence Tomography" in *Science*, 254: 1178-81, 1991 and an article by C. Puliafito et al. entitled "Optical Coherence Tomography of Ocular Diseases" in Slack Inc., 1996). An article by J. A. Izatt et al. entitled "Micrometer-Scale Resolution Imaging of the Anterior Eye In Vivo With Optical Coherence Tomography" in *Arch Ophthalmology*, 112: 1584-89, 1994 suggested using OCT for anterior segment imaging. However, it was only in 2001, with the development of a high speed AC OCT using a 1310 nm wavelength, that good quality, and easy to interpret, images could be produced (see an article by S. Radhakrishnan et al. entitled "Real-Time Optical Coherence Tomography of the Anterior Segment at 1310 nm" in *Arch Ophthalmology*, Vol. 119, pp. 1179-85, August 2001). Compared with other OCTs (see an article by C. Wirbelauer et al. entitled "Experimental Imaging of Intracorneal Ring segments with Optical Coherence Tomography" in *J Refract Surg*, 2003, 19: 367-71; an article by C. Wirbelauer and P. T. Pham entitled "Intraoperative Optical Coherence Pachymetry during Laser in situ Keratomileusis—First clinical experience" in *J Refract. Surg*, 2003, 19: 372-77; and an article by C. Wirbelauer et al. entitled "Imaging scleral expansion bands for presbyopia with optical coherence tomography" in *J Cataract Refract Surg*, 29: 2435-38, 2003), one of the advantages of AC OCT equipment developed by Carl Zeiss Meditec is that it provides a complete image of the anterior segment in one step at a resolution of about 14 μm.

Using the AC OCT, analysis of the eye is a non-contact procedure wherein the patient fixes a target. The target's focus is adjustable using positive or negative lenses to compensate the patient's spherical ametropia and to acquire images in a relaxed situation. It is also possible to defocus the target with negative lenses to induce physiological accommodation of the examined eye. Thus, there is no undue pressure to the anterior segment because the AC OCT is a non-contact system, and the images are obtained in just a few seconds. The image acquisition system produces a video image of an area under study, and saves a predetermined number of images (for example, seven (7)) which are taken at a rate, for example, of 8 images/sec. At the end of the examination, the operator studies the images, and keeps only the best. Further, software recalibrates the chosen images to compensate for induced warping due to optical path length variations through the cornea. Then, after the image is reconstructed, the operator can carry out all desired measurements of the anterior chamber. The following are examples of measurements that may be made: (a) AC diameter; (b) AC depth; (c) corneal pachymetry; (d) pupil diameter; (e) crystalline lens curvature; (f) crystalline lens thickness; and (g) irido-corneal angle opening. Because infrared light beams are stopped by eye pigment, one cannot obtain a view of structures situated behind the pigment epithelium, the iris or the anterior uvea.

Figure 2:
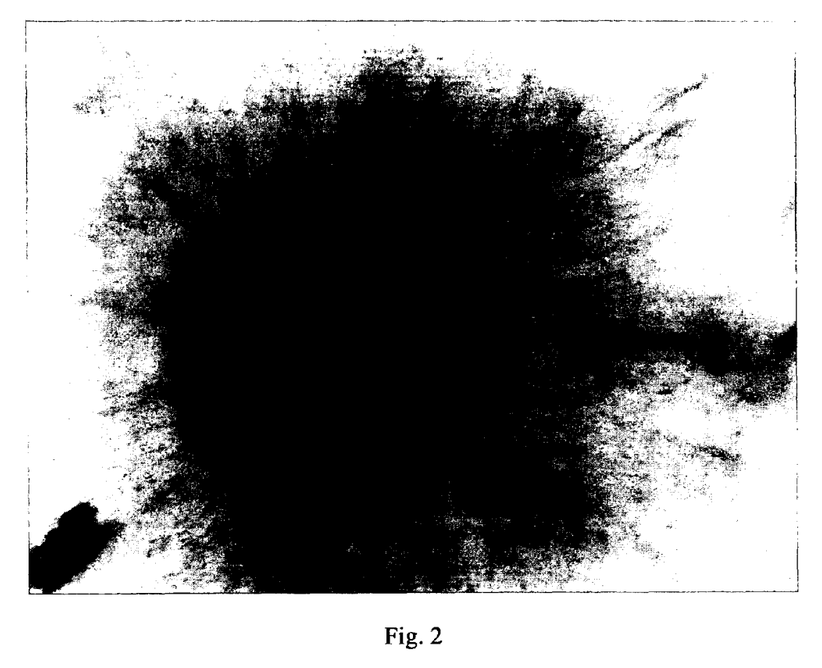
FIG. 2 shows pigment dispersion following a hyperopic ARTISAN™ IOL implant.
Figure 3:
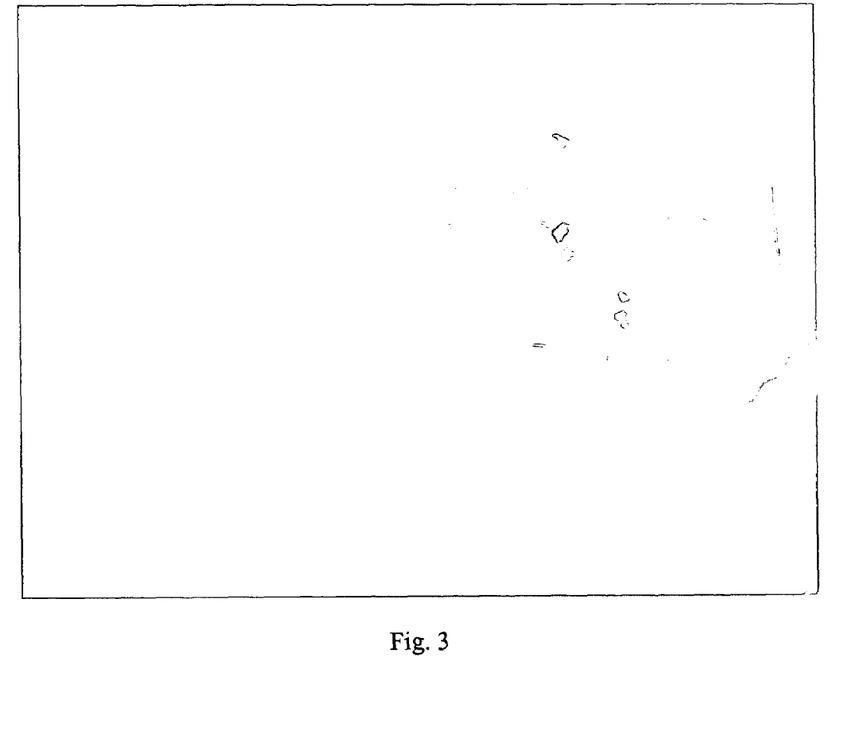
FIG. 3 shows pigment dispersion following a myopic ARTISAN™ IOL implant (note the presence of pigments in the inferior part of the pupil area (←), as well as iris tissue thinning between the iris and the implant (*)
Figure 4:
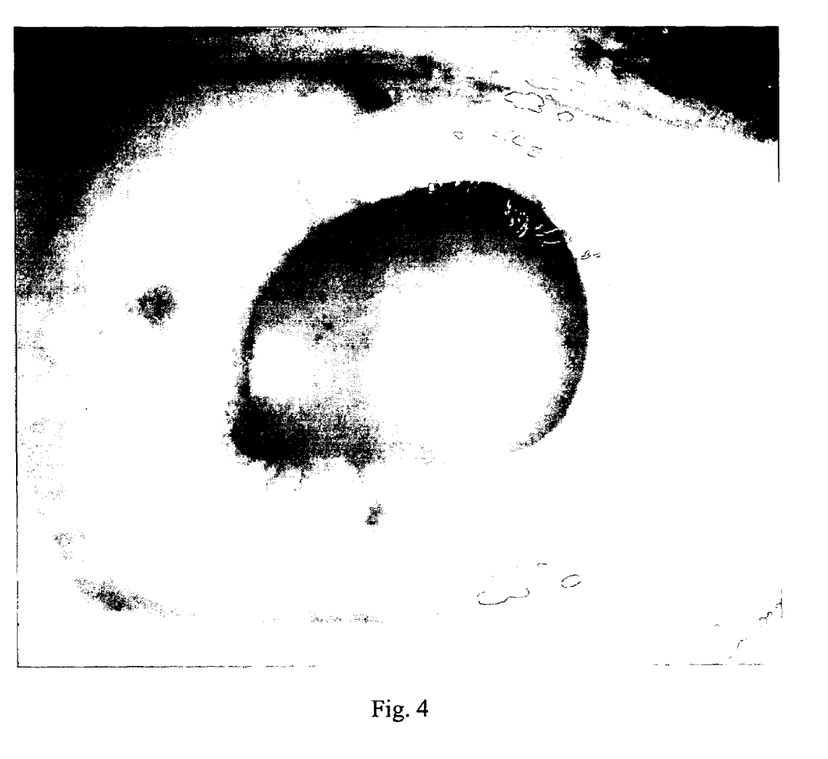
FIG. 4 shows an aspect of the anterior segment following explantation.

In doing the above-described work, the crystalline lens height was measured on the horizontal diameter in a relaxed situation without taking into account its variation during accommodation. Eighty-seven (87) eyes with Artisan™ IOL implants were controlled (forty-three (43) hyperopes and forty-four (44) myopes). This is only 32% of all spherical Artisan™ IOL implants inserted—patient selection was random, and was based only on the fact that they had an appointment to check either their immediate post-operative follow-up or their yearly endothelial control. However, all patients with known pigment dispersion (nine (9) eyes of six (6) patients) were re-examined with the AC OCT. Pigment dispersion observed in this study is different from immediate post-operative inflammatory reactions or uveitis responsible for early development of posterior synechiae or similar complications. These pigment dispersions occur progressively and silently around the pupil, and are accompanied within a few months by uvea ectropion. None of these patients showed signs of immediate acute post-operative inflammatory reactions. Further, over the weeks, these pigment deposits gradually spread over the lower part of the pupil area and can lead to pupillary secclusion with posterior synechiae. FIG. 2 shows pigment dispersion following a hyperopic ARTISAN™ IOL implant; and FIG. 3 shows pigment dispersion following a myopic ARTISAN™ IOL implant (note the presence of pigments in the inferior part of the pupil area (←), as well as iris tissue thinning between the iris and the implant (*). Visual blurring occurs progressively, with a steady drop in visual acuity leading to invalidity. There is no medical treatment, and therapeutic mydriasis has no effect. If there is a loss of visual acuity, the only solution is surgical and consists of implant removal with pre-operative cleansing of the anterior capsule with a smooth cannula. It may also be necessary to treat a resulting or subsequent cataract. In one case, within six (6) months following bilateral surgery, a patient developed a −2 D myopia in one eye only. The implant was exchanged with immediate good optical results despite the persistence of moderate pigment cell deposits in the pupil area. Nine (9) cases of pigment dispersion were observed in six (6) patients. To date, three (3) eyes have been explanted, and the anterior capsule cleansed—FIG. 4 shows an aspect of the anterior segment following explantation. One lens was exchanged. Further, in one case, a cataract was treated by phacoemulsification two months after an Artisan™ IOL implant extraction.

The following is refractive data for the population studied.

Hyperopes: Forty-three (43) eyes of twenty-four (24) patients were studied; eight (8) males and sixteen (16) females; the average age was 44.5±13.2 years and ranged from age 18 to 67. The mean follow-up for ARTISAN™ IOL implant hyperopes was 17.4±13.2 months and ranged from 1 to 47 months; and the mean pre-operative refraction was +4.9 D±1.8 D and ranged from +1.75D to +8.75D. Eight (8) cases of pigment dispersion were observed in five hyperopes.

Myopes: Forty-four (44) eyes of twenty-four (24) patients were studied; ten (10) males and fourteen (14) females; the average age was 36.5±8.7 years and ranged from age 22 to 54. The mean follow up for ARTISAN™ IOL implant myopes was 24.1±15.5 months and ranged from 2 to 46 months); and the mean pre-operative refraction was −10.80 D±6.3 D and ranged from −1.5 D to −29 D. Only one (1) case of pigment dispersion was observed with the myopes.

Methodology: The anterior segment's anatomy was studied postoperatively with AC OCT on the horizontal meridian—unaccommodated eyes without stimulation were studied. In one case only, the examination was carried out without the implant because the patient was explanted before the study began. However, since it was presumed that the anterior segment's anatomic relationships had not been modified by the removal of the implant; the patient was included in the study. With a phakic IOL implant in the anterior chamber, the accuracy of the optical coherence system measurements is only modified by a few microns. The crystalline lens height can either be measured directly from the base of the median to the crystalline lens' anterior pole or by subtracting the distance from the base of the median to the corneal epithelium from the anterior chamber depth (i.e., a distance between the corneal epithelium and the crystalline lens' anterior pole). It may be easier to use the second method since the distances are greater. The second method was used to calculate the crystalline lens height, and the value is given in microns. The different measurements were transferred to Excel software so that the crystalline lens height could be compared with the patients' pre-operative refraction power.

Results: In this series of ARTISAN™ IOL implants, a 5.9% rate of pigment dispersion in hyperopes and a 0.7% rate in all the myopes operated on was observed. The difference between the two groups is significant. This complication is therefore more frequent in hyperopes than in myopes. Mean anterior chamber depth of the entire population studied was 3.54±0.39 mm and ranged from 2.89 mm to 4.68 mm; the hyperopes' mean anterior chamber depth was 3.31±0.27 mm and ranged from 2.89 mm to 3.77 mm; and the myopes' mean anterior chamber depth was 3.77±0.35 mm and ranged from 2.94 mm to 4.68 mm. The mean anterior chamber depth of the nine (9) eyes showing pigment dispersion was 3.05±0.16 mm; and, for the entire eighty-seven (87) eyes studied, the mean length of the crystalline lens height was 298±288 μm and ranged from 276 μm to 1126 μm. It should be noted that in the literature the definition of the anterior chamber depth is not always very clear. In certain cases, it is defined as a distance between the crystalline lens and the corneal endothelium, and in others, it is defined as a distance between the anterior pole and the corneal epithelium—here we have used the latter definition. For the hyperopic patients, the mean length of the crystalline lens height was 461±254 µm and ranged from 50 µm to 1126 µm. For the myopic patients, the mean length of the crystalline lens height was 140±226 µm and ranged from 276 µm to 783 µm. For the patients having developed pigment dispersion, the mean length of the crystalline lens height was 775±204 µm. It was discovered, therefore, that the crystalline lens anterior segment anatomy is different between myopes and hyperopes having been operated on—the myope's anterior chamber is deeper than the hyperope's (3.77 mm vs. 3.31 mm). However, the hyperope's mean crystalline lens height is longer than the myope's (461 µm vs. 140 µm)—once again, there is a significant difference between the hyperope's and myope's crystalline lens anatomy.

Figure 5:
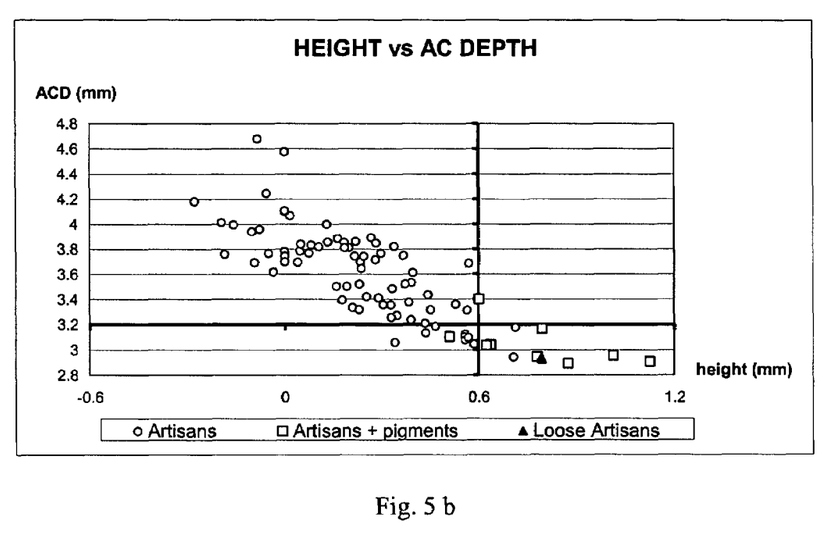
FIG. 5a shows a plot of all eyes in a study comparing crystalline lens height with pre-operative refraction (including those showing pigment dispersion)
FIG. 5b shows a plot of all eyes studied comparing crystalline lens height with anterior chamber depth (including those showing pigment dispersion) (note that 38% of the patients with an anterior chamber depth ≦3.2 mm developed pigment dispersion, and 67% of the patients with a crystalline lens height ≧600 μm developed pigment dispersion)
Figure 5A:
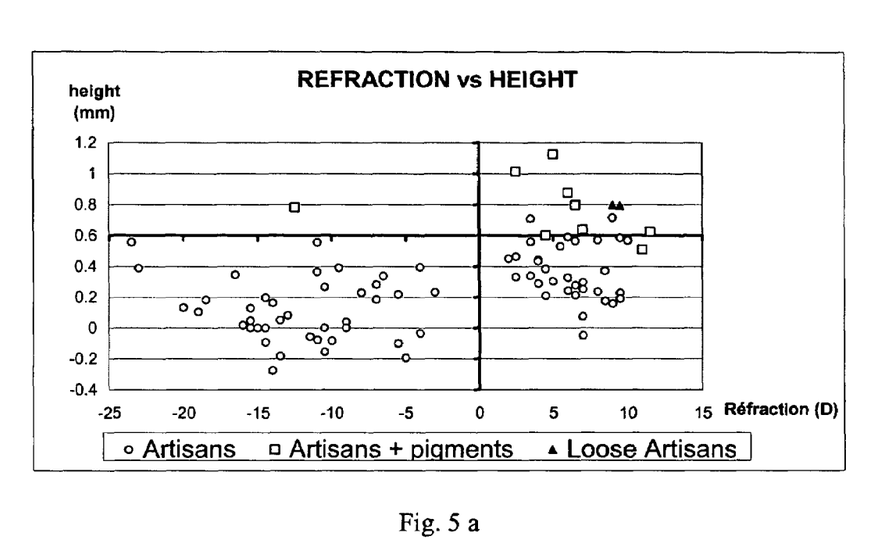
Figure 6:
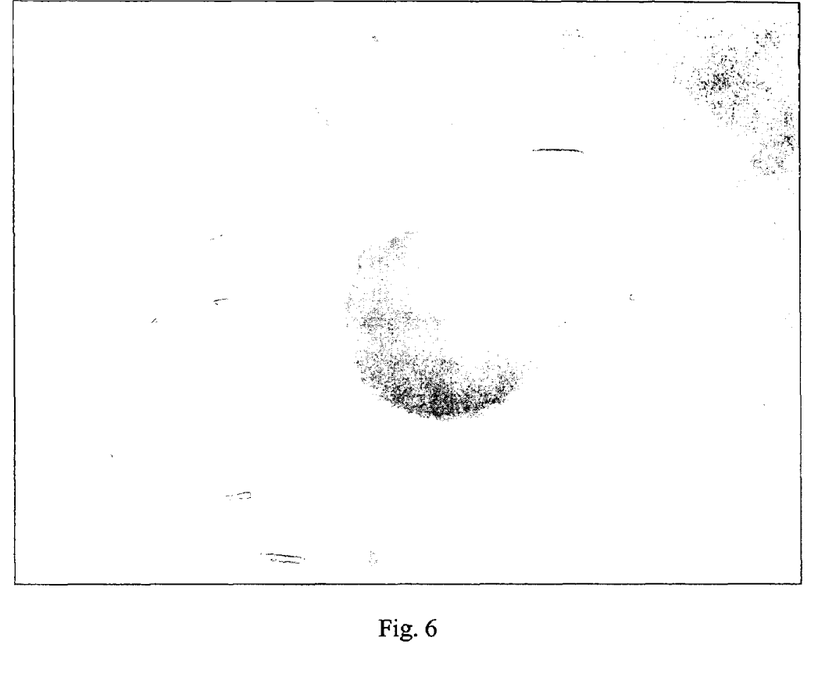
FIG. 6 shows a loosely fixed ARTISAN™ IOL implant where there is no pigment dispersion despite a crystalline lens height of 790 μm.

FIG. 5a shows plot of all eyes studied comparing crystalline lens height with pre-operative refraction (including those showing pigment dispersion—a danger level is 600 µm). FIG. 5b shows a plot of all eyes studied comparing crystalline lens height with anterior chamber depth (including those showing pigment dispersion) (note that 38% of the patients with an anterior chamber depth ≦3.2 mm developed pigment dispersion, and 67% of the patients with a crystalline lens height ≧600 µm developed pigment dispersion). It was noticed that there were eight (8) hyperopes and one (1) myope. Importantly, if one limits the crystalline lens height to 600 µm, referring to FIG. 5b, among the observed population, eight (8) eyes out of twelve (12) (i.e., 67%) developed pigment dispersion. On the other hand, when the crystalline lens height is below 600 µm, one (1) eye out of seventy-five (75) (i.e., 1.3%) developed pigment dispersion. The difference between the two groups is statistically significant. It was also noted that the crystalline lens height of the only myope to have developed pigment dispersion was largely over 600 µm. In addition, it was noticed that using the anterior chamber depth as a criterion is less precise since, referring to FIG. 5b, only 38% of the observed population whose anterior chamber depth was equal to or below 3.2 mm developed pigment dispersion. More recently, both eyes of a hyperopic patient who had not developed pigment dispersion even though the crystalline lens height measured 790 µm was observed. However, the reason pigment dispersion did not develop was the loose fixation of the implant, which was not squashed against the iris but was slightly decentered towards the bottom—FIG. 6 shows a loosely fixed ARTISAN™ IOL implant, and there is no pigment dispersion despite the crystalline lens height of 790 µm. As one can readily appreciate from this and an article by J. L. Alio, M. E. Mulet, and A. M. Shalaby entitled "Artisan phakic iris claw intraocular lens for high primary and secondary hyperopia" in *J Refract Surg*, 2002, 18(6): 697-707, a surgical factor that could favor causing pigment dispersion is pressing the implant against the surface of the iris. However, this is difficult to envisage since the aim of surgery is to avoid having an implant too loose or decentered. On the contrary, a minimum amount of traction on the iris root is necessary for it to remain centered properly. However, this is left to the surgeon's subjective appreciation, and personal dexterity.

Figure 7:
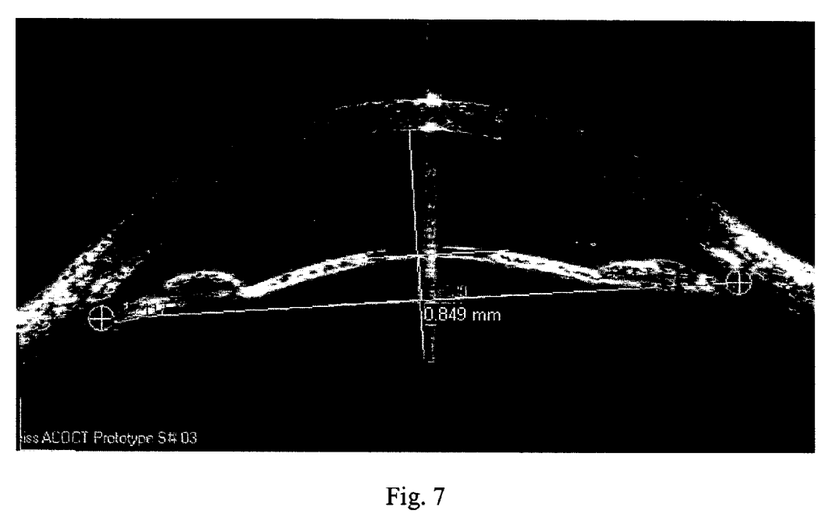
FIG. 7 shows an anterior chamber optical coherence tomography (AC OCT) depiction of pigment dispersion following a myopic ARTISAN™ IOL implant for the same eye shown in FIG. 3 (note compression of iris tissue between the iris and the IOL implant, and note that there is a crystalline lens height after implant of 849 μm)
Figure 8:
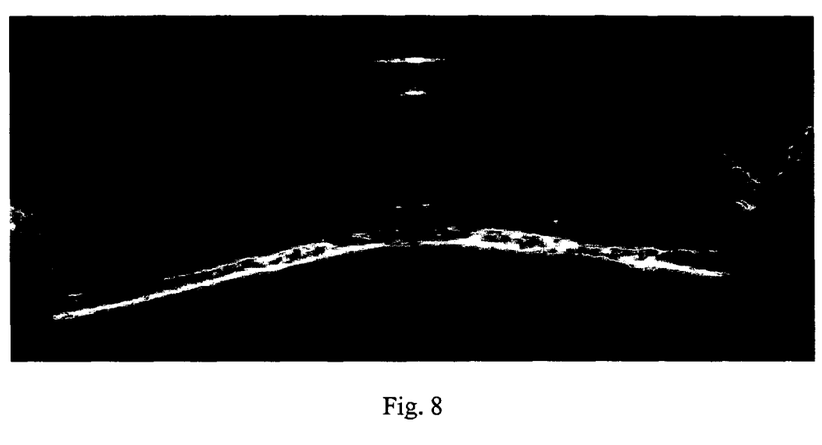
FIG. 8 shows an AC OCT depiction of pigment dispersion (note the presence of pigment dispersion in the pupil area) following a hyperopic ARTISAN™ IOL implant (also note that the iris is laminated between the IOL implant and the crystalline lens).

Few publications mention the existence of pigment dispersion following hyperopic ARTISAN™ IOL implant surgery. In a study to obtain FDA approval, three (3) cases of posterior synechia were observed in fifty-nine (59) hyperopic IOL implants (i.e., 5%)—see the Ophtec website at www.ophtec.com; an article by I. F. Comaish and M. A. Lawless entitled "Phakic Intraocular lenses" in *Curr Opin Ophthalmol*, 13: 7-13, 2002; an article by T. Kohnen et al. entitled "Complications of Phakic Intraocular Lenses" in [D. Hardten, R. Lindstrom, and E. Davis, Eds.] "Phakic Intraocular Lenses, Principles and Practice" Slack Inc., Chapt. 9, pp. 81-96, 2004; and an article by M. M. Braun and E. E. Manche entitled "The Artisan Phakic Intraocular Lens" in [D. Hardten, R. Lindstrom, and E. Davis, Eds.] "Phakic Intraocular Lenses, Principles and Practice" Slack Inc., Chapt. 13, pp. 133-143, 2004. The only anterior segment abnormality referred to in these cases concerns the notion of an iris that is too convex. However this remains a qualitative and subjective notion, and does not provide a precise definition with regard to eye selection. The cause of this pigment dispersion seems to be due to abnormal pressure on the iris which is sandwiched between the crystalline lens and the implant, see FIG. 7 which shows an anterior chamber AC OCT depiction of pigment dispersion following a myopic ARTISAN™ IOL implant for the same eye shown in FIG. 3 (note compression of iris tissue between the iris and the IOL implant, and that there is a crystalline lens height after implant of 849 µm) and FIG. 8 which shows an AC OCT depiction of pigment dispersion (note the presence of pigment dispersion in the pupil area) following a hyperopic ARTISAN™ IOL implant (also note that the iris is laminated between the IOL implant and the crystalline lens). One can readily appreciate that, from a geometric point of view, the further the crystalline lens juts out onto the irido-corneal angle plane, the more the iris will be crushed between the crystalline lens and the implant. The two extremities of the IOL implant are fixed to the periphery of the anterior surface creating traction on the iris root by this forward thrust, and since it is not extensible, the iris will be crushed between the anterior surface of the crystalline lens and the posterior surface of the implant.

Using phakic IOLs for surgical treatment of high myopia is much more frequent than for treatment of hyperopia. This explains a lack of literature on the subject. An article by R. Saxena, M. Landesz, B. Noordzij, and G. P. M. Luyten entitled "Three-year Follow-up of the Artisan Phakic Intraocular Lens for Hypermetropia" in *Ophthalmology*, Vol. 110, No. 7, pp. 1391-95, July 2003 reported four cases of pigment dispersion in twenty-six (26) hyperopic eyes (i.e., 15%)—pre-operative examinations included A-Scan biometry. Two (2) patients experienced bilateral complications. The anterior chamber depth of patient 1 was 3.30 mm, and for patient 2 was 3.00 mm. The convex irides of patient 1 were considered the reason for the complications. For patient 2, no explanation was given by the authors. An article by I. F. Comaish and M. A. Lawless entitled "Phakic Intraocular lenses" in *Curr Opin Ophthalmol*, 13: 7-13, 2002 reported three (3) cases of pigment dispersion and pupillary membrane secondary to an "iris touch." In their study, this problem appeared to be more frequent with hyperopes than with myopes. They give no explanation for this complication, and neither does an article by T. Kohnen et al. entitled "Complications of Phakic Intraocular Lenses" in [D. Hardten, R. Lindstrom, and E. Davis, Eds.] "Phakic Intraocular Lenses, Principles and Practice" Slack Inc., Chapt. 9, pp. 81-96, 2004. In addition, an article by J. L. Alio, M. E. Mulet, and A. M. Shalaby entitled "Artisan phakic iris claw intraocular lens for high primary and secondary hyperopia" in *J Refract Surg*, 2002, 18(6): 697-707 did not report any cases of pigment dispersion, but did note pigments on the implant and posterior synechia within a certain lapse of time which is not specified—there might have been some confusion with the existence of anterior uveitis.

In light of the above, one ought to study a profile of the anterior segment with modern imaging techniques (as described above, using a Scheimpflug technique, an UHF ultrasound scanner, or AC OCT equipment) during a pre-operative examination when considering a phakic IOL implant. For example, these techniques are crucial for angle-supported implants in evaluating the anterior chamber's internal diameter and for determining a minimum clearance distance between the implant and the corneal endothelium. In addition, in accordance with one or more embodiments of the present invention, an objective criterion is utilized which is related to crystalline lens height. The use of this objective criterion enabled a determination of the risk of pigment dispersion following ARTISAN™ IOL implant surgery (67% of population observed) with a great deal more accuracy than the use of the anterior chamber depth, since only 38% of patients with an anterior chamber depth less than or equal to 3.2 mm developed pigment dispersion. Thus, in accordance with one or more embodiments of the present invention, a method for determining whether to perform a phakic intraocular lens implant procedure comprises: (a) obtaining an image of an anterior segment of an eye; (b) determining a distance from a crystalline lens to another part of an anterior chamber from the image; and (c) comparing the distance with a predetermined value. Preferably, the distance is a length between an anterior pole of the crystalline lens and a line connecting a first 3:00 o'clock angle recess to a second, opposing, 9:00 o'clock angle recess, and the predetermined value is in a range from about 500 μm to about 700 μm.

In accordance with one or more further embodiments of the present invention, the crystalline lens height may be used to predict how long the IOL implant can remain safely in place. As disclosed in an article by J. F. Koretz, S. A. Strenk, L. M. Strenk, and J. J. Semmlow entitled "Scheimpflug and high-resolution magnetic resonance imaging of the anterior segment: a comparative study" in *J Opt Soc Am A*, Vol. 21, No. 3. pp. 346-354, March 2004 and in an article by G. Baïkoff, E. Lutun, J. Wei, and C. Ferraz entitled "Contact between 3 phakic intraocular lens models and the crystalline lens: An anterior chamber optical coherence tomography study" in *J Cataract Refract Surg;* 30: 2007-2012, September 2004 there is an 18 μm to 20 μm annual statistical forward progression of the crystalline lens' anterior pole. Using this information, and in accordance with one or more embodiments of the present invention, one can calculate a tolerance safety period of time (T) for an IOL implant such as, for example and without limitation, an ARTISAN™ IOL implant, beginning after the day of surgery. This is done as follows.

Let: T=number of safe years for an IOL implant, S=a maximum safe value of the crystalline lens height (in microns), Δ=a yearly reduction of anterior chamber depth or a yearly progression of a crystalline lens' anterior pole (in microns), and F=a measured crystalline lens height (measured in microns on the day of pre-operative examination). Using these parameters, in accordance with one or more embodiments of the present invention, one obtains:

$$T=(S-F)/\Delta$$

Illustratively, assume that: (a) a maximum safe value of the crystalline lens height is 600 μm, i.e., S=600 μm; (b) a yearly reduction of anterior chamber depth is 20 μm per year, i.e., Δ=20 μm; and (c) the crystalline lens height measured during the pre-operative examination is 200 μm, i.e., F=200 μm.

Then: T=(600−200)/20=400/20=20 years.

Although various embodiments that incorporate the teachings of the present invention have been shown and described in detail herein, those skilled in the art can readily devise many other varied embodiments that still incorporate these teachings.

What is claimed is:

1. A method for determining whether to perform a phakic intraocular lens implant procedure, which method comprises:
    obtaining an image of at least a portion of an anterior segment of an eye;
    determining a distance from a crystalline lens to another part of an anterior chamber from the image; and
    comparing the distance with a predetermined value in determining whether to perform the phakic intraocular lens procedure;
    wherein the image is a cross-sectional image substantially along an anterior-posterior axis of the eye; and
    wherein the distance is a length between an anterior pole of the crystalline lens and a line connecting a first angle recess to a second, opposing angle recess.

2. The method of claim 1 wherein the line is a horizontal line connecting a 3:00 o'clock angle recess to a 9:00 o'clock angle recess.

3. A method for determining whether to perform a phakic intraocular lens implant procedure, which method comprises:
    obtaining an image of at least a portion of an anterior segment of an eye;
    determining a distance from a crystalline lens to another part of an anterior chamber from the image; and
    comparing the distance with a predetermined value in determining whether to perform the phakic intraocular lens procedure;
    wherein the image is a cross-sectional image substantially along an anterior-posterior axis of the eye; and
    wherein the distance is a length between a base of a median and an anterior pole of the crystalline lens.

4. The method of claim 3 wherein the distance is determined by subtracting a length between a base of the median and a corneal epithelium or endothelium from an anterior chamber depth.

5. A method for determining whether to perform a phakic intraocular lens implant procedure, which method comprises:
    obtaining an image of at least a portion of an anterior segment of an eye;
    determining a distance from a crystalline lens to another part of an anterior chamber from the image; and
    comparing the distance with a predetermined value in determining whether to perform the phakic intraocular lens procedure;
    wherein the distance is a length between an anterior pole of the crystalline lens and a line connecting a first angle recess to a second opposing angle recess, and the predetermined value is in a range from about 500 to about 700 microns.

6. A method for determining whether to perform a phakic intraocular lens implant procedure, which method comprises:
    obtaining an image of at least a portion of an anterior segment of an eye;

determining a distance from a crystalline lens to another part of an anterior chamber from the image; and comparing the distance with a predetermined value in determining whether to perform the phakic intraocular lens procedure;

wherein said image is obtained using an optical technique;

wherein said optical technique is optical coherence tomography; and wherein the predetermined value is approximately 600 microns.

7. A method for determining a quantitative criterion for phakic intraocular lens implantation which comprises:

determining a distance from an anterior pole of a crystalline lens to a line connecting a first angle recess to a second, opposing angle recess.

8. The method of claim 7 wherein determining comprises: obtaining an image of an anterior segment of an eye.

9. A method for predicting a length of time over which a phakic intraocular lens can remain safely in place after its implant, which method comprises:

determining a difference between a predetermined value and a pre-operatively measured crystalline lens height; and determining the length of time utilizing: (a) the difference and (b) a progression rate of an anterior pole of the crystalline height.

10. The method of claim 9 wherein the second determining comprises dividing the difference by the progression rate.

* * * * *